US006242382B1

(12) United States Patent
Bratz et al.

(10) Patent No.: US 6,242,382 B1
(45) Date of Patent: Jun. 5, 2001

(54) SOLID MIXTURES BASED ON SULFONYLUREAS AND ADJUVANTS

(75) Inventors: Matthias Bratz; Karl-Friedrich Jäger, both of Limburgerhof; Rainer Berghaus, Speyer; Hans Ziegler, Mutterstadt; Thomas Kröhl, Mainz; Adolf Parg, Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/381,548

(22) PCT Filed: Mar. 12, 1998

(86) PCT No.: PCT/EP98/01441

§ 371 Date: Sep. 21, 1999

§ 102(e) Date: Sep. 21, 1999

(87) PCT Pub. No.: WO98/42192

PCT Pub. Date: Oct. 1, 1998

(30) Foreign Application Priority Data

Mar. 24, 1997 (DE) ............................... 197 12 225

(51) Int. Cl.⁷ ........................... A01N 43/64; A01N 43/54; A01N 43/66
(52) U.S. Cl. ........................... 504/133; 504/134; 504/136; 504/231; 504/239
(58) Field of Search .................................... 504/133, 134, 504/136, 231, 239

(56) References Cited

U.S. PATENT DOCUMENTS 4,936,899 6/1990 Schulz et al. ............................. 71/73
5,236,887 * 8/1993 Noveroske ........................... 504/105
5,679,128 * 10/1997 Latting et al. ........................... 71/49

FOREIGN PATENT DOCUMENTS 313 317 7/1989 (EP) .
554 015 8/1993 (EP) .

OTHER PUBLICATIONS

ANNP–Seizieme Conf. Du column–Journees Int. sur la lutte contre les mauvaises herbes 1995, S. 469–474; DPX–KG 691—A new surfactant for . . . , Green et al.

Weed Tech., Jan.–Mar., 1995, vol. 9, No. 1, 689–695, Nalewaja et al.

Weed Sci, 1994, vol. 42:82–85, Dunne et al. Primary Linear Alcohol Ethoxylates as Adjuvants . . .

Weed Tech. 1993, vol. 7:633–640, Green et al. Surfactant Structure and Concentaration . . .

JP62/084004, Abstract.
JP08/014603, Abstract.
JP63/023806, Abstract.

* cited by examiner

Primary Examiner—S. Mark Clardy
Assistant Examiner—Alton Pryor
(74) Attorney, Agent, or Firm—Keil & Weinkauf

(57) ABSTRACT

A solid ixture comprising
a) an active ingredient from the group of the sulfonylureas and
b) an alkyl ether of a copolymer of $C_2$–$C_4$-alkylene oxides.

7 Claims, No Drawings

SOLID MIXTURES BASED ON SULFONYLUREAS AND ADJUVANTS

This application is a 371 of PCT/EP98/01441 filed Mar. 12, 1998.

The present invention relates to solid mixture ased on sulfonylureas and adjuvants.

Sulfonylureas (referred to as "SU" hereinafter) are a group of highly active herbicides which are employed in many fields of crop protection.

Due to the mechanism of active ingredient uptake via the leaf, the action of SU can be improved by adding surfactants such as wetters to the spray mixture (cf. Green et al.,ANPP, Seiziéme conference du columa—Journées internationales sur la lutte contre les mauvaises herbes 1995, pp. 469–474; "DPX-KG 691—A new surfactant for sulfonyl urea herbicides").

Wetters which are described in the literature as being particularly suitable are, inter alia, oil adjuvants (Nalejewa et al., Weed Technol. 1995, 9, pp. 689–695) or alcohol ethoxylates (see above, and Dunne et al., Weed Science 1994, 42, pp. 82–85; Green, Weed Technol. 1993, 7, pp. 633–640). In agricultural practice, these substances are added to the spray mixture by the practitioner in the form of tank mix additives. The mixture of SU herbicide and surfactant is prepared in the spray tank only a short time before use.

An example of a commercially available product is a double pack with the trade name CATO® (Du Pont de Nemours), which is composed of 25% strength water-dispersible granules of the active ingredient rimsulfuron (component A) and a separately packaged wetter (component B) composed of a mixture of 2-butoxyethanol, polyethoxylated tallowamine and nonylphenyl polyethylene glycol ether. For use, the two components are mixed in the spray tank as described above.

It would be desirable, under practice conditions, to be able to employ readymixes which already comprise an activity-enhancing wetter so as to avoid the problem of mixing immediately prior to use. This would allow logistical problems and mixing errors to be avoided when making the spray mixture. Furthermore, readymixes are generally advantageous from the point of view of application when designing and disposing of the packaging.

It is furthermore known from the literature that formulations which comprise sulfonylureas are problematic as regards the stability of the active ingredients, since the active ingredient may undergo decomposition under unfavorable conditions in the course of time. This means that the desired herbicidal action is lost. The tendency to decomposition is also a problem with a view to the registration requirements since, for registration, the stability of crop protection agents in formulations must meet certain requirements.

JP-A 62/084004 describes the use of calcium carbonate and sodium tripolyphosphate for stabilizing SU-comprising formulations.

JP-A 63/023806 describes how the problem can be solved by using specific carriers and vegetable oils for the preparation of solid SU-comprising formulations. JP-A 08/104603 describes similar effects when using epoxydized natural oils. A shared feature of the two applications mentioned above is the incorporation of vegetable oils in the solid formulation so as to utilize the activity-enhancing effects of these substances, which act as adjuvants, in addition to an improved stability.

When incorporating vegetable oils into liquid formulations (as a rule suspension concentrates), similar effects are exploited (cf. EP-A 313317 and EP-A 554015).

It is also known from the prior art that alcohol alkoxylates together with sulfonylureas can be employed as tank mix additives.

It is an object of the present invention to provide solid formulations with sulfonylureas as active ingredients which already comprise adjuvants in the solid formulation and which are superior to solid formulations known to date.

We have found that this object is achieved according to the invention by solid mixtures which comprise a) a sulfonylurea and b) an adjuvant from the group of the alkyl ethers of copolymers of $C_2$–$C_4$-alkylene oxides.

Surprisingly, it has been found that, when using alkyl ethers of copolymers of $C_2$–$C_4$-alkylene oxides as wetters in SU-comprising solid-substance formulations, pronounced stabilization of the active ingredient occurs in comparison with other wetters. This effect is especially surprising because structurally related compounds such as fatty alcohol ethoxylates (see Comparison Examples 1 and 2) and ethylene oxide/propylene oxide block copolymers do not show this behavior, but, in contrast, even lead to degradation of the active ingredient. The advantageous effect can be observed especially when water-soluble inorganic salts such as ammonium sulfate are present in addition to herbicidally active ingredients. Stabilization becomes particularly pronounced when the wetter is employed at the concentration required for the biological action.

Storage-stable readymixes with good biological action can be obtained by mixing the SU with other active ingredients, alkyl ethers of copolymers of $C_2$–$C_4$-alkylene oxides and ammonium sulfate.

We have furthermore found processes for the preparation of the solid mixtures according to the invention and their use as crop protection products for controlling undesirable harmful plants.

Suitable as sulfonylurea a) are generally compounds with the structural unit

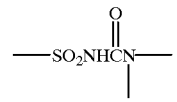

Preferred are SU of the following structures I:

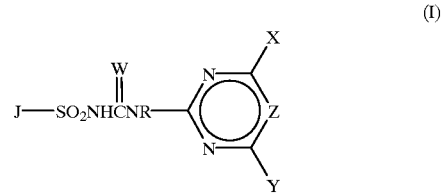

(I)

where J has the following meanings:

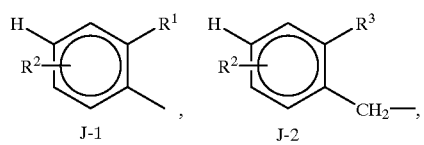

-continued

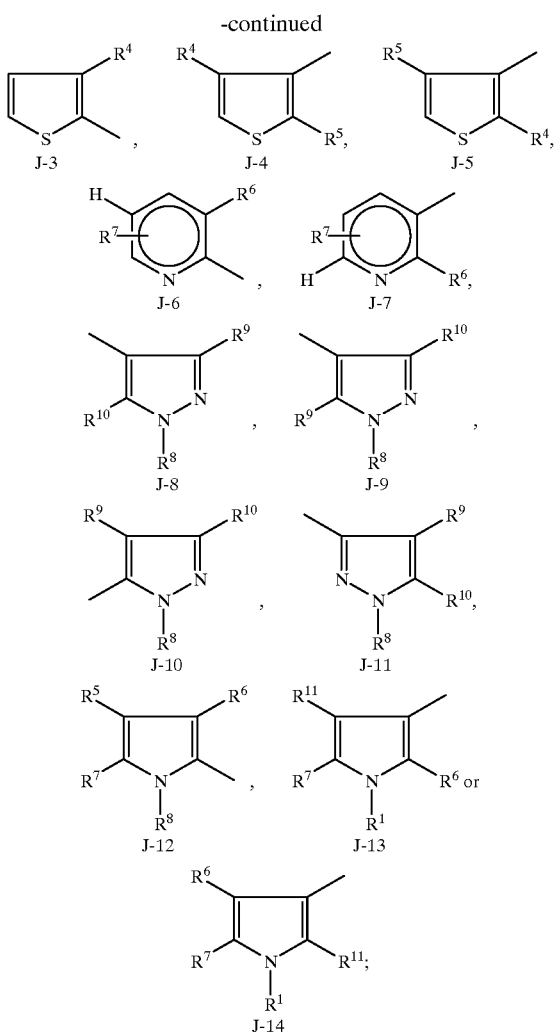

where the substituents R to $R^{18}$ have the following meanings:

R: H or $CH_3$;
$R^1$: F, Cl, Br, $NO_2$, $C_1$–$C_4$-alkyl, $C_1$–$C_4$-haloalkyl, $C_3$–$C_4$-cycloalkyl, $C_2$–$C_4$-haloalkenyl, $C_1$–$C_4$-alkoxy, $C_1$–$C_4$-haloalkoxy, $C_2$–$C_4$-alkoxyalkoxy, $CO_2R^{12}$, $C(O)NR^{13}R^{14}$, $SO_2NR^{15}R^{16}$, $S(O)_nR^{17}$, $C(O)R^{18}$, $CH_2CN$ or L;
$R^2$: H, F, Cl, Br, CN, $CH_3$, $OCH_3$, $SCH_3$, $CF_3$ or $OCF_2H$;
$R^3$: Cl, $NO_2$, $CO_2CH_3$, $CO_2CH_2CH_3$, $SO_2N(CH_3)_2$, $SO_2CH_3$, $SO_2CH_2CH_3$, $OCH_3$, or $OCH_2CH_3$;
$R^4$: $C_1$–$C_3$-alkyl, $C_1$–$C_4$-haloalkyl, $C_1$–$C_4$-alkoxy, $C_2$–$C_4$-haloalkenyl, F, Cl, Br, $NO_2$, $CO_2R^{12}$, $C(O)NR^{13}R^{14}$, $SO_2NR^{15}R^{16}$, $S(O)_nR^{17}$, $C(O)R^{18}$ or L;
$R^5$: H, F, Cl, Br or $CH_3$;
$R^6$: $C_1$–$C_4$-alkyl, $C_1$–$C_4$-alkoxy, $C_2$–$C_4$-haloalkenyl, F, Cl, Br, $CO_2R^{12}$, $C(O)NR^{13}R^{14}$, $SO_2NR^{15}R^{16}$, $S(O)_nR^{17}$, $C(O)R^{18}$ or L;
$R^7$: H, F, Cl, $CH_3$ or $CF_3$;
$R^8$: H, $C_1$–$C_4$-alkyl or pyridyl;
$R^9$ is $C_1$–$C_4$-alkyl, $C_1$–$C_4$-alkoxy, F, Cl, Br, $NO_2$, $CO_2R^{12}$, $SO_2NR^{15}R^{16}$, $S(O)_nR^{17}$, $OCF_2H$, $C(O)R^{18}$, $C_2$–$C_4$-haloalkenyl or L;
$R^{10}$: H, Cl, F, Br, $C_1$–$C_4$-alkyl or $C_1$–$C_4$-alkoxy;
$R^{11}$: H, $C_1$–$C_4$-alkyl, $C_1$–$C_4$-alkoxy, $C_2$–$C_4$-alkoxy; haloalkenyl, F, Cl, Br, $CO_2R^{12}$, $C(O)NR^{13}R^{14}$, $SO_2NR^{15}R^{16}$, $S(O)_nRl^7$, $C(O)R^{18}$ or L;

$R^{12}$: $C_1$–$C_4$-alkyl, unsubstituted or substituted by halogen, $C_1$–$C_4$-alkoxy or CN, allyl or propargyl;
$R^{13}$: H, $C_1$–$C_4$-alkyl or $C_1$–$C_4$-alkoxy;
$R^{14}$: $C_1$–$C_4$-alkyl;
$R^{15}$: H, $C_1$–$C_4$-alkyl, $C_1$–$C_4$-alkoxy, allyl or cyclopropyl;
$R^{16}$: H or $C_1$–$C_4$-alkyl;
$R^{17}$: $C_1$–$C_4$-alkyl, $C_1$–$C_4$-haloalkyl, allyl or propargyl;
$R^{18}$: $C_1$–$C_4$-alkyl, $C_1$–$C_4$-haloalkyl or $C_3$–$C_5$-cycloalkyl, unsubstituted or substituted by halogen;
n is 0.1 or 2;
L has the structure II

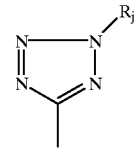

(II)

where
Rj is H or $C_1$–$C_3$-alkyl;
W is 0 or S;
X is H, $C_1$–$C_4$-alkyl, $C_1$–$C_4$-alkoxy, $C_1$–$C_4$-haloalkoxy, $C_1$–$C_4$-haloalkyl, $C_1$–$C_4$-haloalkylthio, $C_1$–$C_4$-alkylthio, halogen, $C_2$–$C_5$-alkoxyalkyl, $C_2$–$C_5$-alkoxyalkoxy, amino, $C_1$–$C_3$-alkylamino or di($C_1$–$C_3$-alkyl)amino;
Y is H, $C_1$–C4-alkyl, $C_1$–$C_4$-alkoxy, $C_1$–$C_4$-haloalkoxy, $C_1$–$C_4$-alkylthio, $C_1$–$C_4$-haloalkylthio, $C_2$–$C_5$-alkoxyalkyl, $C_2$–$C_5$-alkoxyalkoxy, amino, $C_1$–$C_3$-alkylamino, di($C_1$–$C_3$-alkyl)-amino, $C_3$–$C_4$-alkenyloxy, $C_3$–$C_4$-alkanyloxy, $C_2$–$C_5$-alkylthioalkyl, $C_2$–$C_5$-alkylsulfinylalkyl, $C_2$–$C_5$-alkylsulfonylalkyl, $C_1$–$C_4$-haloalkyl, $C_2$–$C_4$-alkenyl, $C_3$–$C_5$-cycloalkyl, azido, fluorine or cyano;
Z is CH or N;
and the agriculturally useful salts thereof.

Some suitable SU together with their INN (International Nonproprietary Name) in accordance with Pesticide Manual may be mentioned below:

amidosulfuron;
azimsulfuron (N-[[[(4,6-dimethoxy-2-pyrimidinyl) amino]-carbonyl]-1-methyl-4-(2-methyl-2H-tetrazol-5-yl)-1H-pyrazole-5-sulfonamide);
bensulfuron-methyl (methyl 2-[[[[[(4,6-dimethoxy-2-pyrimidinyl)amino]carbonyl]amino]sulfonyl]methyl] benzoate);
ethyl 2-[[[[(4-chloro-6-methoxy-2-pyrimidinyl)-amino] carbonyl]amino]sulfonyl]benzoate (chlorimuron-ethyl);
2-chloro-N-[[(4-methoxy-6-methyl-1,3,5-triazin-2-yl) amino]carbonyl]benzenesulfonamide (chlorsulfuron);
chlorsulfoxim;
cinosulfuron;
cyclosulfamuron;
ethametsulfuron-methyl (methyl 2-[[[[[4-ethoxy-6-(methylamino)-1,3,5-triazin-2-yl]amino]carbonyl] amino]sulfonyl]-benzoate);
ethoxysulfuron;
flazasulfuron;
flupyrsulfuron (methyl 2-[[[[(4,6-dimethoxy-2-pyrimidinyl)-amino]carbonyl]amino]sulfonyl]-6-(trifluoromethyl)-3-pyridine-carboxylate);

halosulfuron-methyl;

imazasulfuron;

methyl 2-[[[[(4-methoxy-6-methyl-1,3,5-triazin-2-yl)amino]carbonyl]amino]sulfonyl]benzoate (metsulfuron-methyl);

nicosulfuron (2-[[[[(4,6-dimethoxy-2-pyrimidinyl)amino]-carbony]amino]sulfonyl]-N,N-dimethyl-3-pyridinecarboxamide);

oxasulfuron;

primisulfuron (methyl 2-[[[[[4,6-bis(difluoromethoxy)-2-pyrimidinyl]amino]carbonyl]amino]sulfonyl]benzoate);

prosulfuron;

pyrazosulfuron-ethyl (ethyl 5-[[[[(4,6-dimethoxy-2-pyrimidinyl)amino]carbonyl]amino]sulfonyl]-1-methyl-1H-pyrazole-4-carboxylate);

rimsulfuron (N-[[4,6-dimethoxy-2-pyrimidinylamino]carbonyl]-3-(ethylsulfonyl)-2-pyridinesulfonamide);

sulfosulfuron;

sulfometuron-methyl (methyl 2-[[[[(4,6-dimethyl-2-pyrimidinyl)amino]carbonyl]amino]sulfonyl]benzoate);

thifensulfuron-methyl (methyl-3-[[[[(4-methoxy-6-methyl-1,3,5-triazin-2-yl)amino]carbonyl]amino]sulfonyl]-2-thiophenecarboxylate);

2-(2-chloroethoxy)-N-[[(4-methoxy-6-methyl-1,3,5-triazin-2-yl)amino]carbonyl]benzenesulfonamide (triasulfuron);

tribenuron-methyl (methyl 2-[[[[N-(4-methoxy-6-methyl-1,3,5-triazin-2-yl)-N-methylamino]carbonyl]amino]sulfonyl]benzoate); and triflusulfuron-methyl (methyl 2-[[[[[4-(dimethylamino)-6-(2,2,2-trifluoroethoxy)-1,3,5-triazin-2-yl]amino]carbonyl]-amino]sulfonyl]-3-methylbenzoate).

Expecially preferred are sulfonylureas of the general formula III (corresponds to formula I where $J=J_1$), as they are disclosed, for example, in EP-A 388 873, EP-A 559 814, EP-A 291 851 and EP-A 446 743:

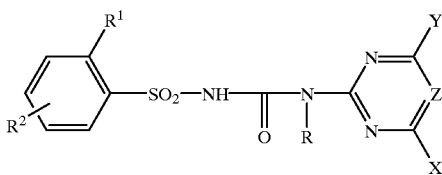

(III)

where the substituents have the following meanings:

$R^1$ is $C_1$–$C_4$-alkyl which can have attached to it one to five of the following groups: methoxy, ethoxy, $SO_2CH_3$, cyano, chlorine, fluorine, $SCH_3$, $S(O)CH_3$; halogen;

a group $ER^{19}$ where E is ), S or $NR^{20}$;

$COOR^{12}$;

$NO_2$;

$S(O)_nR^{17}$, $SO_2NR^{15}R^{16}$, $CONR^{13}R^{14}$;

$R^2$ is hydrogen, methyl, halogen, methoxy, nitro, cyano, trifluoromethyl, trifluoromethoxy, difluoromethoxy or methylthio, Y is F, $CF_3$, $CF_2Cl$, $CF_2H$, $OCF_3$, $OCF_2Cl$, $C_1$–$C_4$-alkyl or $C_1$–$C_4$-alkoxy;

X is $C_1$–$C_2$-alkoxy, $C_1$–$C_2$-alkyl, $C_1$–$C_2$-alkylthio, $C_1$–$C_2$-alkylamino, di-$C_1$–$C_2$-alkylamino, halogen, $C_1$–$C_2$-haloalkyl, $C_1$–$C_2$-haloalkoxy, R is hydrogen or methyl;

$R^{19}$ is $C_1$–$C_4$-alkyl, $C_2$–$C_4$-alkenyl, $C_2$–$C_4$-alkynyl or $C_3$–$C_6$-cycloalkyl, each of which can have attached to it 1 to 5 halogen atoms. In the event that E is O or $NR^{20}$, $R^{19}$ is furthermore also methylsulfonyl, ethylsulfonyl, trifluoromethylsulfonyl, allylsulfonyl, propargylsulfonyl or dimethylsulfamoyl;

$R^{20}$ is hydrogen, methyl or ethyl;

$R^{12}$ is a $C_1$–$C_4$-alkyl group which can have attached to it up to three of the following radicals: halogen, $C_1$–$C_4$-alkoxy, allyl or propargyl;

$R^{17}$ is a $C_1$–$C_4$-alkyl group which can have attached to it one to three of the following radicals: halogen, $C_1$–$C_4$-alkoxy, allyl or propargyl;

$R^{15}$ is hydrogen, a $C_1$–$C_2$-alkoxy group or a $C_1$–$C_4$-alkyl group;

$R^{16}$ is hydrogen or a $C_1$–$C_4$-alkyl group, n is 1 or 2

Z is N, CH.

Particularly preferred sulfonylureas of the formula III are those of the formula I where J is $J_1$ and the remaining substituents have the following meanings:

$R^1$ $CO_2CH_3$, $CO_2C_2H_5$, $CO_2iC_3H_7$, $CF_3$, $CF_2H$; $OSO_2CH_3$, $OSO_2N(CH_3)_2$, Cl $NO_2$, $SO_2N(CH_3)_2$, $SO_2CH_3$ and $N(CH_3)SO_2CH_3$, $R^2$ hydrogen, Cl, F or $C_1$–$C_2$-alkyl, Y $CF_2H$, $OCF_3$, $OCF_2Cl$, $CF_2Cl$, $CF_3$ or F, X $OCH_3$, $OC_2H_5$, $OCF_3$, $OCF_2Cl$; $CF_3$, Cl, F, $NH(CH_3)$, $N(CH_3)_2$ or $C_1$–$C_2$-alkyl, $R^5$ hydrogen, and Z N or CH.

Very especially preferred compounds of the formula III are compiled in the table which follows.

TABLE

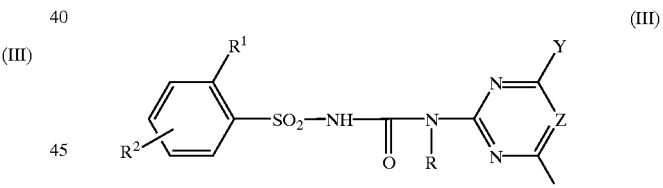

(III)

| No. | $R^1$ | $R^2$ | R | Y | X | Z |
|---|---|---|---|---|---|---|
| 1 | $CO_2CH_3$ | H | H | $OCF_2Cl$ | $OCH_3$ | CH |
| 2 | $CO_2C_2H_5$ | H | H | $OCF_2Cl$ | $OCH_3$ | CH |
| 3 | $CO_2iC_3H_7$ | H | H | $OCF_2Cl$ | $OCH_3$ | CH |
| 4 | $NO_2$ | H | H | $OCF_2Cl$ | $OCH_3$ | CH |
| 5 | $SO_2CH_3$ | H | H | $OCF_2Cl$ | $OCH_3$ | CH |
| 6 | $SO_2N(CH_3)_2$ | H | H | $OCF_2Cl$ | $OCH_3$ | CH |
| 7 | Cl | H | H | $OCF_2Cl$ | $OCH_3$ | CH |
| 8 | $N(CH_3)SO_2CH_3$ | H | H | $OCF_2Cl$ | $OCH_3$ | CH |
| 9 | $OSO_2CH_3$ | H | H | $OCF_2Cl$ | $OCH_3$ | CH |
| 10 | $OSO_2N(CH_3)_2$ | H | H | $OCF_2Cl$ | $OCH_3$ | CH |
| 11 | $CF_3$ | H | H | $OCF_2Cl$ | $OCH_3$ | CH |
| 12 | $CF_2H$ | H | H | $OCF_2Cl$ | $OCH_3$ | CH |
| 13 | $CO_2CH_3$ | H | H | $OCF_3$ | $OCH_3$ | CH |
| 14 | $CO_2C_2H_5$ | H | H | $OCF_3$ | $OCH_3$ | CH |
| 15 | $CO_2iC_3H_7$ | H | H | $OCF_3$ | $OCH_3$ | CH |
| 16 | $NO_2$ | H | H | $OCF_3$ | $OCH_3$ | CH |
| 17 | $SO_2CH_3$ | H | H | $OCF_3$ | $OCH_3$ | CH |
| 18 | $SO_2N(CH_3)_2$ | H | H | $OCF_3$ | $OCH_3$ | CH |
| 19 | Cl | H | H | $OCF_3$ | $OCH_3$ | CH |
| 20 | $N(CH_3)SO_2CH_3$ | H | H | $OCF_3$ | $OCH_3$ | CH |
| 21 | $OSO_2CH_3$ | H | H | $OCF_3$ | $OCH_3$ | CH |

TABLE-continued

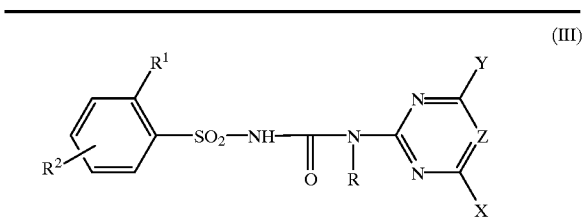

(III)

| No. | R¹ | R² | R | Y | X | Z |
|---|---|---|---|---|---|---|
| 22 | $OSO_2N(CH_3)_2$ | H | H | $OCF_3$ | $OCH_3$ | CH |
| 23 | $CF_3$ | H | H | $OCF_3$ | $OCH_3$ | CH |
| 24 | $CF_2H$ | H | H | $OCF_3$ | $OCH_3$ | CH |
| 25 | $CO_2CH_3$ | H | H | F | $OCH_3$ | CH |
| 26 | $CO_2C_2H_5$ | H | H | F | $OCH_3$ | CH |
| 27 | $CO_2iC_3H_7$ | H | H | F | $OCH_3$ | CH |
| 28 | $NO_2$ | H | H | F | $OCH_3$ | CH |
| 29 | $SO_2CH_3$ | H | H | F | $OCH_3$ | CH |
| 30 | $SO_2N(CH_3)_2$ | H | H | F | $OCH_3$ | CH |
| 31 | Cl | H | H | F | $OCH_3$ | CH |
| 32 | $N(CH_3)SO_2CH_3$ | H | H | F | $OCH_3$ | CH |
| 33 | $OSO_2CH_3$ | H | H | F | $OCH_3$ | CH |
| 34 | $OSO_2N(CH_3)_2$ | H | H | F | $OCH_3$ | CH |
| 35 | $CF_3$ | H | H | F | $OCH_3$ | CH |
| 36 | $CF_2H$ | H | H | F | $OCH_3$ | CH |
| 37 | $CO_2CH_3$ | H | H | $CF_3$ | $OCH_3$ | N |
| 38 | $CO_2C_2H_5$ | H | H | $CF_3$ | $OCH_3$ | N |
| 39 | $CO_2iC_3H_7$ | H | H | $CF_3$ | $OCH_3$ | N |
| 40 | $NO_2$ | H | H | $CF_3$ | $OCH_3$ | N |
| 41 | $SO_2CH_3$ | H | H | $CF_3$ | $OCH_3$ | N |
| 42 | $SO_2N(CH_3)_2$ | H | H | $CF_3$ | $OCH_3$ | N |
| 43 | Cl | H | H | $CF_3$ | $OCH_3$ | N |
| 44 | $N(CH_3)SO_2CH_3$ | H | H | $CF_3$ | $OCH_3$ | N |
| 45 | $OSO_2CH_3$ | H | H | $CF_3$ | $OCH_3$ | N |
| 46 | $OSO_2N(CH_3)_2$ | H | H | $CF_3$ | $OCH_3$ | N |
| 47 | $CF_3$ | H | H | $CF_3$ | $OCH_3$ | N |
| 48 | $CF_2H$ | H | H | $CF_3$ | $OCH_3$ | N |
| 49 | $CO_2CH_3$ | H | H | $CF_3$ | $OCH_3$ | CH |
| 50 | $CO_2C_2H_5$ | H | H | $CF_3$ | $OCH_3$ | CH |
| 51 | $CO_2iC_3H_7$ | H | H | $CF_3$ | $OCH_3$ | CH |
| 52 | $NO_2$ | H | H | $CF_3$ | $OCH_3$ | CH |
| 53 | $SO_2CH_3$ | H | H | $CF_3$ | $OCH_3$ | CH |
| 54 | $SO_2N(CH_3)_2$ | H | H | $CF_3$ | $OCH_3$ | CH |
| 55 | Cl | H | H | $CF_3$ | $OCH_3$ | CH |
| 56 | $N(CH_3)SO_2CH_3$ | H | H | $CF_3$ | $OCH_3$ | CH |
| 57 | $OSO_2CH_3$ | H | H | $CF_3$ | $OCH_3$ | CH |
| 58 | $OSO_2N(CH_3)_2$ | H | H | $CF_3$ | $OCH_3$ | CH |
| 59 | $CF_3$ | H | H | $CF_3$ | $OCH_3$ | CH |
| 60 | $CF_2H$ | H | H | $CF_3$ | $OCH_3$ | CH |
| 61 | $CO_2CH_3$ | H | H | $CF_2H$ | $OCH_3$ | N |
| 62 | $CO_2C_2H_5$ | H | H | $CF_2H$ | $OCH_3$ | N |
| 63 | $CO_2iC_3H_7$ | H | H | $CF_2H$ | $OCH_3$ | N |
| 64 | $NO_2$ | H | H | $CF_2H$ | $OCH_3$ | N |
| 65 | $SO_2CH_3$ | H | H | $CF_2H$ | $OCH_3$ | N |
| 66 | $SO_2N(CH_3)_2$ | H | H | $CF_2H$ | $OCH_3$ | N |
| 67 | Cl | H | H | $CF_2H$ | $OCH_3$ | N |
| 68 | $N(CH_3)SO_2CH_3$ | H | H | $CF_2H$ | $OCH_3$ | N |
| 69 | $OSO_2CH_3$ | H | H | $CF_2H$ | $OCH_3$ | N |
| 70 | $OSO_2N(CH_3)_2$ | H | H | $CF_2H$ | $OCH_3$ | N |
| 71 | $CF_3$ | H | H | $CF_2H$ | $OCH_3$ | N |
| 72 | $CF_2H$ | H | H | $CF_2H$ | $OCH_3$ | N |
| 73 | $CO_2CH_3$ | H | H | $CF_2H$ | $OCH_3$ | CH |
| 74 | $CO_2C_2H_5$ | H | H | $CF_2H$ | $OCH_3$ | CH |
| 75 | $CO_2iC_3H_7$ | H | H | $CF_2H$ | $OCH_3$ | CH |
| 76 | $NO_2$ | H | H | $CF_2H$ | $OCH_3$ | CH |
| 77 | $SO_2CH_3$ | H | H | $CF_2H$ | $OCH_3$ | CH |
| 78 | $SO_2N(CH_3)_2$ | H | H | $CF_2H$ | $OCH_3$ | CH |
| 79 | Cl | H | H | $CF_2H$ | $OCH_3$ | CH |
| 80 | $N(CH_3)SO_2CH_3$ | H | H | $CF_2H$ | $OCH_3$ | CH |
| 81 | $OSO_2CH_3$ | H | H | $CF_2H$ | $OCH_3$ | CH |
| 82 | $OSO_2N(CH_3)_2$ | H | H | $CF_2H$ | $OCH_3$ | CH |
| 83 | $CF_3$ | H | H | $CF_2H$ | $OCH_3$ | CH |
| 84 | $CF_2H$ | H | H | $CF_2H$ | $OCH_3$ | CH |
| 85 | $CO_2CH_3$ | H | H | $CF_2Cl$ | $OCH_3$ | N |
| 86 | $CO_2C_2H_5$ | H | H | $CF_2Cl$ | $OCH_3$ | N |
| 87 | $CO_2iC_3H_7$ | H | H | $CF_2Cl$ | $OCH_3$ | N |
| 88 | $NO_2$ | H | H | $CF_2Cl$ | $OCH_3$ | N |
| 89 | $SO_2CH_3$ | H | H | $CF_2Cl$ | $OCH_3$ | N |
| 90 | $SO_2N(CH_3)_2$ | H | H | $CF_2Cl$ | $OCH_3$ | N |
| 91 | Cl | H | H | $CF_2Cl$ | $OCH_3$ | N |
| 92 | $N(CH_3)SO_2CH_3$ | H | H | $CF_2Cl$ | $OCH_3$ | N |
| 93 | $OSO_2CH_3$ | H | H | $CF_2Cl$ | $OCH_3$ | N |
| 94 | $OSO_2N(CH_3)_2$ | H | H | $CF_2Cl$ | $OCH_3$ | N |
| 95 | $CF_3$ | H | H | $CF_2Cl$ | $OCH_3$ | N |
| 96 | $CF_2H$ | H | H | $CF_2Cl$ | $OCH_3$ | N |
| 97 | $CO_2CH_3$ | 3-F | H | Cl | $OCH_3$ | CH |
| 98 | $CF_2CF_3$ | H | H | $CH_3$ | $OCH_3$ | N |
| 99 | $CF_2CF_3$ | H | H | $CH_3$ | $OCH_3$ | N |
| 100 | $SO_2C_2H_5$ | H | H | F | $OCH_3$ | CH |

Naturally, mixtures of a plurality of sulfonylureas may also be employed as component a).

The solid formulations according to the invention comprise, as component b), one or more alkyl ethers of copolymers of $C_2$–$C_4$-alkylene oxides, preferably of random or block copolymers of ethylene oxide and propylene oxide. As a rule, the alkyl group in the ether radical has 10 to 25, preferably 12 to 20, C atoms and is perferably linear. The molar ratio of ethylene oxide to propylene oxide units is not subject to any particular restriction and is normally in the range of from 1:10 to 10:1, preferably of from 1:5 to 5:1 and in particular of from 1:3 to 3:1. In the case of block copolymers, the block length is generally in a range of from 2–100 units per block.

Such products are known to those skilled in the art and described in the literature. The reference to Mccutheon's Emulsifiers and Detergents, Volumes 1 and 2 (1994), North American Edition, McCutheon Division, Glen Rock, USA, and "Surfactants in Europe", 2nd Edition 1989, Terg Data, Darlington, UK, are only exemplary.

Suitable commercially available products are, for example, Antarox® BO (by Rhône Poulenc), Emulsogen® V2436 (by Hoechst), Dehypon® LS and LT (by Henkel), Synperionic® LF (by ICI Specialty Chemicals) and, in particular, the products of the Plurafac® LF series by BASF Aktiengesellschaft.

The amount of component a) in the solid mixtures according to the invention is generally in the range of from 0.5 to 75% by weight, preferably of from 1 to 25% by weight, based on the total weight of the formulation.

The amount of component b) is generally in a range from 1 to 75, in particular 1 to 50, and especially preferably 5 to 25% by weight, based on the total weight of the formulation.

The solid mixtures according to the invention may also comprise, in addition to components a) and b), other active ingredients which can be mixed with, or act synergistically with, sulfonylureas. Such products are known to those skilled in the art and described in the literature. The following groups of other active ingredients may be mentioned by way of example, using their INN:

c1: 1,3,4-Thiadiazoles:
  buthidazole, cyprazole;
c2: Amides:
  allidochlor (CDAA), benzoylprop-ethyl, bromobutide, chlorthiamid, dimepiperate, dimethenamid, diphenamid, etobenzanid (benzchlomet), flamprop-methyl, fosamin, isoxaben, monalide, naptalame, pronamid (propyzamid), propanil;
c3: Aminophosphoric acids
  bilanafos (bialaphos), buminafos, glufosinate-ammonium, glyphosate, sulfosate
c4: Aminotriazoles:
  amitrol;
c5: Anilides:
  anilofos, mefenacet, thiafluamide;
c6: Aryloxyalkanoic acids
  2,4-D, 2,4-DB, clomeprop, dichlorprop, dichlorprop-P, (2,4-DP-P), fenoprop (2,4,5-TP), fluoroxypyr, MCPA, MCPB, mecoprop, mecoprop-P, napropamide, napropanilide, triclopyr;
c7: Benzoic acids:
  chloramben, dicamba;
c8: Benzothiadiazinones:
  bentazone;
c9: Bleachers:
  clomazone (dimethazone), diflufenican, fluorochloridone, flupoxam, fluridone, pyrazolate, sulcotrione (chlormesulone), isoxaflutol, 2-(2'-chloro-3'-ethoxy-4'-ethylsulfonylbenzoyl)-4-methylcyclo-hexane-1,3-dione;
c10: Carbamates:
  asulam, barban, butylate, carbetamide, chlorbufam, chlorpropham, cycloate, desmedipham, di-allate, EPTC, esprocarb, molinate, orbencarb, pebulate, phenisopham, phenmedipham, propham, prosulfocarb, pyributicarb, sulf-allate (CDEC), terbucarb, thiobencarb (benthiocarb), tiocarbazil, tri-allate, vernolate;
c11: Quinolinecarboxylic acids
  quinclorac, quinmerac;
c12: Chloroacetanilides:
  acetochlor, alachlor, butachlor, butenachlor, diethatyl-ethyl,
  dimethachlor, dimethenamide (cf. also category c2), metazachlor, metolachlor, pretilachlor, propachlor, prynachlor, terbuchlor, thenylchlor, xylachlor;
c13: Cyclohexenones:
  alloxydim, caloxydim, clethodim, cloproxydim, cycloxydim, sethoxydim, tralkoxydim, 2-{1-[(2-(4-chlorophenoxy)propyloxy-imino]butyl}-3-hydroxy-5-(2H-tetrahydrothiopyran-3-yl)-2-cyclohexen-1-one;
c14: Dichloropropionic acids:
  dalapon;
c15: Dihydrobenzofurans:
  ethofumesate;
c16: Dihydrofuran-1-ones:
  flurtamone;
c17: Dinitroanilines:
  benefin, butralin, dinitramin, ethalfluralin, fluchloralin, isopropalin, nitralin, oryzalin, pendimethalin, prodiamine, profluralin, trifluralin;
c18: Dinitrophenols:
  bromofenoxim, dinoseb, dinoseb-acetate, dinoterb, DNOC;
c19: Diphenyl ethers:
  acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen, oxyfluorfen;
c20: Dipyridylenes:
  cyperquat, difenzoquat-methylsulfate, diquat, paraquat-dichloride;
c21: Ureas:
  benzthiazuron, buturon, chlorbromuron, chloroxuron, chlortoluron, cumyluron, dibenzyluron, cycluron, dimefuron, diuron, dymron, ethidimuron, fenuron, fluormeturon, isoproturon, isouron, karbutilate, linuron, methabenzthiazuron, metobenzuron, metoxuron, monolinuron, monuron, neburon, siduron, tebuthiuron, trimeturon;
c22: Imidazoles:
  isocarbamid;
c23: Imidazolinones:
  imazamethapyr, imazapyr, imazaquin, imazethabenz-methyl (imazame), imazethapyr, imazamox;
c24: Oxadiazoles:
  methazole, oxadiargyl, oxadiazone;
c25: Oxiranes:
  tridiphane
c26: Phenols:
  bromoxynil, ioxynil;
c27: Phenoxypropionic esters
  clodinafop, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofoptefuryl;
c28: Phenylacetic acids:
  chlorfenac (fenac);
c29: Phenylpropionic acids:
  chlorfenprop-methyl;
c30: Protoporphyrinogen-IX oxydase inhibitors:
  benzofenap, cinidon-ethyl, flumiclorac-pentyl, flumioxazin, flumipropyn, flupropacil, fluthiacet-methyl, pyrazoxyfen, sulfentrazone, thidiazimine, carfentrazone, azafenidin;
c31: Pyrazoles:
  nipyraclofen;
c32: Pyridazines:
  chloridazon, maleic hydrazide, norflurazon, pyridate;
c33: Pyridinecarboxylic acids:
  clopyralid, dithiopyr, picloram, thiazopyr;
c34: Pyrimidyl ethers:
  pyrithiobac-acid, pyrithiobac-sodium, pyriminobac-methyl, bispyribenzoxim, bispyribac-sodium;
c35: Sulfonamides:
  flumetsulam, metosulam, cloransulam-methyl, diclosulam;
c36: Triazines:
  ametryn, atrazine, aziprotryn, cyanazine, cyprazine, desmetryn, dimethamethryn, dipropetryn, eglinazine-ethyl, hexazinone, procyazine, prometon, prometryn, propazine, secbumeton, simazine, simetryn, terbumeton, terbutryn, terbuthylazine, trietazine, dimesyflam;
c37: Triazinones:
  ethiozin, metamitron, metribuzin;
c38: Triazolecarboxamides:

triazofenamid;

c39: Uracils:

bromacil, lenacil, terbacil;

c40: Various others:

benazolin, benfuresate, bensulide, benzofluor, butamifos, cafenstrole, chlorthal-dimethyl (DCPA), cinmethylin, dichlobenil, endothal, fluorbentranil, mefluidide, perfluidone, piperophos, diflufenzopyr, diflufenzopyr-sodium or the ecologically friendly salts of the abovementioned groups of active ingredients.

Examples of other preferred active ingredients c) are:

bromobutide, dimethenamide, isoxaben, propanil, glufosinate-ammonium, glyphosate, sulfosate, mefenacet, thiafluamide, 2,4-D, 2,4-DB, dichlorprop, dichlorprop-P, dichlorprop-P(2,4-DP-P), fluoroxopyr, MCPA, mecoprop, mecoprop-P, dicamba, bentazone, clomazone, diflufenican, sulcotrione, isoxaflutole, phenmedipham, thiobencarb, quinclorac, quinmerac, acetochlor, alachlor, butachlor, metazachlor, metolachlor, pretilachlor, butroxydim, caloxydim, clethodim, cycloxydim, sethoxydim, tralkoxydim, 2-{1-[2-(4-chlorophenoxy)propyloxyimino]butyl}-3-hydroxy-5-(2H-tetrahydrothiopyran-3-yl)-2-cyclohexen-1-one, pendimethalin, acifluorfen-sodium, bifenox, fluoroglycofen-ethyl, fomesafen, lactofen, chlortoluron, cycluron, dymron, isoproturon, metabenzthiazuron, imazaquin, imazamox, imazethabenz-methyl, imazethapyr, bromoxynil, ioxynil, clodinafop, cyhalofop-butyl, fenoxyprop-ethyl, fenoxaprop-p-ethyl, haloxyfop-p-methyl, cinidon-ethyl, flumiclorac-pentyl, carfentrazone, flumipropyn, fluthiacet-methyl, pyridate, clopyralid, bispyribac-sodium, pyriminobac-methyl, flumetsulam, metosulam, atrazine, cyanazine, terbutylazine, benazolin, benfuresate, cafenstrole, cinmethylin, ammonium-bentazone, cloquintocet, diflufenzopyr, diflufenzopyr-sodium, pyraflufen-ethyl.

Particularly preferred are the following compounds c):

2,4-D, dichlorprop-P, MCPA, mecoprop-P, dicamba, bentazone, diflufenican, sulcotrione, quinclorac, caloxydim, cycloxydim, sethoxydim, 2-{1-[2-(4-chlorophenoxy)propyloxyimino]butyl}-3-hydroxy-5-(2H-tetrahydro-thiopyran-3-yl)-2-cyclohexen-1-one, acifluorfen-sodium, fluoroglycofen-ethyl, bromoxynil, fenoxyprop-ethyl, cinidon-ethyl, atrazine, terbuthylazine, ammonium-bentazone, cloquintocet, thiafluamid, isoxaflutole, diflufenzopyr, diflufenzopyr-Na, carfentrazone, imazamox.

Very especially preferred are the following compounds c):

2,4-D, dichlorprop-P, mecoprop-P, MCPA, ammonium-bentazone, bentazone, diflufenican, quinclorac, 2-{1-[2-(4-chlorophenoxy)propyloxyimino]butyl}-3-hydroxy-5-(2H-tetrahydrothiopyran-3-yl)-2-cyclohexen-1-one, caloxydim, cycloxydim, sethoxydim, fluoroglycofen-ethyl, cinidon-ethyl, atrazine and terbuthylazine, dicamba, diflufenzopyr, diflufenzopyr-sodium.

The amount of the other active ingredients c)—if present—is generally in a range of from 0.5 to 75, preferably of from 1 to 60% by weight of the formulation.

In addition to the above-described components a), b) and c), the solid mixtures according to the invention may additionally comprise formulation auxiliaries which are known per se.

Suitable as surfactants are the alkali metal, alkaline earth metal or ammonium salts of aromatic sulfonic acids, eg. ligno-, phenol-, naphthalene- and dibutylnaphthalene-sulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenol-sulfonic acid with formaldehyde, condensates of phenol with formaldehyde and sodium sulfite, polyoxyethylene octylphenyl ether, ethoxylated isooctyl-, octyl-or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or mixtures of these.

If surfactants are used concomitantly, the amount of these is generally in the range of from 0.5 to 25% by weight, based on the total weight of the solid mixture.

The solid mixtures according to the invention may also be used together with carrier materials. Examples of carriers which may be mentioned are:

mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or mixtures of these.

Further additives which can be employed in amounts which are customary per se are also:

Water-soluble compounds or salts such as:

sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate;

Binders such as:
polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or mixtures of these;

lubricants such as:
magnesium stearate, sodium stearate, talc or polyethylene glycol, or mixtures of these;

antifoams such as:
silicone emulsions, long-chain alcohols, phosphoric esters, acetylene diols, fatty acids or organofluorine compounds, and complexing agents such as:
salts of ethylenediaminetetraacetic acid (EDTA), salts of trinitrilotriacetic acid or salts of polyphosphoric acids, or mixtures of these.

The solid mixtures according to the invention can be prepared in the form of powders, granules, briquettes, tablets and similar formulation variants. Apart from powders, granules are especially preferred. The powders may be water-soluble or water-dispersible powders. The granules may be water-soluble or water-dispersible granules for use in spray application, or so-called granules for spreading, for direct application. In general, the average particle size of the granules is between 200 µm and 2 mm.

The granule formulations obtained are dust-free, free-flowing, non-caking products which are readily soluble or dispersible in cold water.

Due to their characteristics, the products can be packaged readily in relatively large amounts. Apart from containers such as polymer, paper or laminated sacks or bags, they can be handled in cardboard boxes or other bulk containers. To avoid further exposure of the user, it is possible to package the products in water-soluble film bags, for example polyvinyl alcohol film bags, which are introduced directly into the spray tank, where they dissolve. The following may be employed, inter alia, for such water-soluble films: polyvinyl alcohol or cellulose derivatives such as methylcellulose, methylhydroxypropylcellulose or carboxymethylcellulose. Since the product is packaged in portions which are the right size for use, the user no longer comes into contact with it. The water-soluble bags are preferably packaged in an external sheath which is impermeable to water vapor, such as polyethylene film, polyethylene-laminated paper or aluminum foil.

The solid formulations according to the invention can be prepared by a variety of processes known to those skilled in the art.

Preferred preparation processes for the abovementioned formulations are extruder granulation, spray drying, fluidized-bed agglomeration, mixer granulation and disk granulation.

Especially suitable is fluidized-bed granulation (FBG). Depending on the desired composition of the formulation, an aqueous solution, emulsion or suspension which comprises all components of the formula is sprayed and agglomerated in an FBG apparatus.

Alternatively, it is also possible to introduce salts of active ingredients and/or inorganic ammonium salts into the apparatus and spray them with a solution or emulsion/suspension of the remaining constituents of the formula, during which process agglomerates are formed. It is furthermore possible to apply aqueous solutions, emulsions or suspensions which comprise certain components of the formula in succession to granules of the active ingredient, a salt of the active ingredient and/or an inorganic ammonium salt, thereby obtaining various coating layers.

In general, the granules are dried sufficiently during fluidized-bed granulation. However, it may be advantageous to follow the granulation step by a separate drying step in the same or in a separate dryer. After granulation/drying, the product is cooled and screened.

Another especially suitable process is extruder granulation. Preferably suitable for extruder granulation are basket, radial or dome extruders in which the granule undergoes little compaction.

To carry out the granulation process, a mixture of solids is made into a paste with a granulation liquid in a suitable mixer until an extrudable mass is formed. The latter is extruded in one of the abovementioned extruders. Aperture sizes of between 0.3 and 3 mm are used for the extrusion (preferably 0.5–1.5 mm). Mixtures of active ingredients, formulation auxiliaries and salts which may or may not be soluble in water act as mixtures of solids. The former are generally pre-ground. In some cases it suffices when only the substances which are not soluble in water are pre-ground in suitable mills.

Suitable granulation liquids are water, the alkylene oxide alkyl ethers as set forth in the invention, or aqueous solutions of these. Furthermore suitable are aqueous solutions of inorganic salts, non-ionic surfactants, anionic surfactants, solutions of binders such as polyvinylpyrrolidone, polyvinyl alcohol, carboxymethylcellulose, starch, vinylpyrrolidine/vinyl acetate copolymers, sugars, dextrin or polyethylene glycol. After extruder granulation, the resulting granules are dried and, if appropriate, screened in order to separate coarse particles and fines.

COMPARISON EXAMPLE 1

A premix consisting of:

| | |
|---|---|
| 73.1 g | of SU 1 (Compound No. 47 of Table 1) (technical grade 95.7%) |
| 8 g | of Tamol ® NH |
| 17.9 g | of Ufoxane ® 3A | was mixed and ground in a high-speed rotor mill.
Furthermore,

| | |
|---|---|
| 7.1 g | of premix 1 |
| 5 g | of Extrusil ® (Degussa) |
| 77.9 g | of ammonium sulfate | were mixed, in a Moulinette kitchen blender, with 28 g of Lutensol$^R$ ON 80 in the form of a 50% strength aqueous solution. The resulting mass was extruded by means of an extruder (KAR-75, Fitzpatrick Europe). The resulting moist granules were dried in a drying oven.

COMPARISON EXAMPLE 2

A premix consisting of:

| | |
|---|---|
| 73.1 g | of SU 1 (technical grade 95.7%) |
| 8 g | of Tamol ® NH |

-continued

| | |
|---|---|
| 17.9 g | of Ufoxane ® 3A | was mixed and ground in a high-speed rotor mill. Furthermore,

| | |
|---|---|
| 7.1 g | of premix |
| 15 g | of Extrusil ® (Degussa) |
| 77.9 g | of ammonium sulfate | were mixed, in a Moulinette kitchen blender, with 29 g of Lutensol ON 60 in the form of a 50% strength aqueous solution. The resulting mass was extruded by means of an extruder (KAR-75, Fitzpatrick Europe). The resulting moist granules were dried in a drying oven.

COMPARISON EXAMPLE 3

A premix consisting of:

| | |
|---|---|
| 73.1 g | of SU 1 (technical grade 95.7%) |
| 6 g | of Tamol ® NH |
| 17.9 g | of Ufoxane ® 3A | was mixed and ground in a high-speed rotor mill. Furthermore,

| | |
|---|---|
| 7.1 g | of premix |
| 5 g | of Tamol ® NH |
| 58.9 g | of ammonium sulfate |
| 1 g | of antifoam emulsion SRE |
| 3 g | of Sipernat ® 22 |
| 25 g | of Pluronic ® PE 6800 | were made into a paste with 21 ml of water in a Moulinette kitchen blender. The resulting mass was extruded by means of an extruder (KAR-75, Fitzpatrick Europe). The resulting granules were dried in a drying oven.

EXAMPLE 1

A premix consisting of:

| | |
|---|---|
| 225 g | of distilled water |
| 13 g | of SU 1 (technical grade 95.7%) |
| 13 g | of Tamol ® NH |
| 26 g | of Ufoxane ® 3A |
| 2.1 g | of antifoam emulsion SRE |
| 37.5 g | of Extrusil ® |
| 62.5 g | of Wettol ® LF 700 | was mixed and ground in a bead mill. The resulting suspension was used later as the spray mixture.

100 g of pulverulent ammonium sulfate were introduced into a laboratory-size fluidized-bed granulator Combi Coata®, by Niro Aeromatic. A two-substance nozzle was arranged above the fluidizing floor. What had been introduced was fluidized using air at 120° C. The spray pressure of the two-substance nozzle was adjusted to 200 kPa, the spray mixture was sprayed into the fluidized bed, and the water evaporated. The resulting granules were screened over a screen with a mesh size of 0.2 mm in order to remove the fines.

The table which follows illustrates the components used in the examples:

TABLE 2

| Name | chemical name | Obtained from |
|---|---|---|
| Tamol ® NH | naphthalenesulfonic acid/formaldehyde condensate | BASF AG |
| Ufoxane ® 3A | sodium lignosulfonate | Borregaard |
| Extrusil ® | highly disperse calcium silicate | Degussa |
| Sipernat ® 22 | highly disperse silica | Degussa |
| Antifoam SRE | silicone oil emulsion | Wacker-Chemie |
| Lutensol ® ON 60 | fatty alcohol ethoxylate (6EO) | BASF AG |
| Lutensol ® ON 80 | fatty alcohol ethoxylate (8EO) | BASF AG |
| Aerosol ® OT-B | dioctyl sulfosuccinate | American Cyanamid |
| Morwet ® EFW | dispersant blend | Witco Corp. |
| Pluronic ® PE 6800 | EO/PO block copolymer | BASF AG |
| Plurafac ® LF 700 | alkylated EO/PO block copolymer | BASF AG |
| SU-1 | Comp. 47 of Table 1 | |
| Clefoxydim | 2-{1-[2-(4-chlorophenoxy)propyloxamino]butyl}-5-tetrahydrothiopyran-3-ylcyclohexane-1,3-dione | |
| Cinidon-ethyl | ethyl (z)-2-chloro-3-[2-chloro-5-(4,5,6,7-tetra-hydro-1,3-dioxoisoindole-dion-2-yl)-phenyl]acrylate | |

Test Methods

The content of active ingredient SU in the formulations in accordance with the above examples was determined in each case by means of quantitative HPLC and is shown in Table 3 in percent.

Storage Stability Tests:

To test for storage stability, samples of the formulation in question of Examples 1–4 and the Comparison Examples 1 to 3 were stored in tightly sealed glass containers at the temperature given in each case (54° C. or 50° C.) for a specific time (14 days or 30 days). The samples are subsequently examined and compared with the comparison value at the beginning of storage (zero value). The content of active ingredient is given as relative amount of SU based on the zero value (in percent). The storage tests were carried out by a method similar to CIPAC MT 46. Here, the long-term stability of a product is estimated by short-term storage at elevated temperature.

Table 3 shows the results obtained from determining the storage stability of the solid mixtures of Examples 1–4 and Comparison Examples 1–3.

TABLE 3

| Ex. No. | Adjuvant | Content of active ingredient in % by weight | relative content of active ingredient SU after 14 days, 54° C. |
|---------|----------|---------------------------------------------|----------------------------------------------------------------|
| V1 | Lutensol ® ON 80 | 3.2 | 16 |
| V2 | Lutensol ON 60 ® | 3.2 | 14 |
| V3 | Pluronic ® PE 6800 | 3.7 | 3 |
| 1 | Plurafac ® LF 700 | 5.5 | 83 |

The results show the superior characteristics of the solid mixtures according to the invention.

We claim:

1. A solid mixture comprising
   a) an active ingredient from the group of the sulfonylureas and
   b) an alkyl ether of a copolymer of $C_2$–$C_4$-alkylene oxides.

2. A solid mixture as claimed in claim 1, comprising a sulfonylurea of the formula III

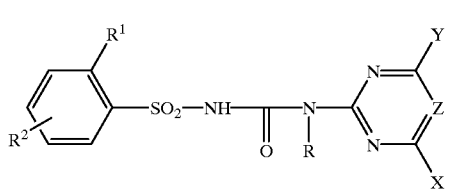

(III)

where the substituents have the following meanings;

$R^1$ is $C_1$–$C_4$alkyl which can have attached to it one to five of the following groups: methoxy, ethoxy, $SO_2CH_3$, cyano, chlorine, fluorine, $SCH_3$, $S(O)CH_3$;
halogen;
a group $ER^{19}$ where E is O, S or $NR^{20}$;
$COOR^{12}$;
$NO_2$;
$S(O)_nR^{17}$, $SO_2NR^{15}R^{16}$, $CONR^{13}R^{14}$;

$R^2$ is hydrogen, methyl, halogen, methoxy, nitro, cyano, trifluoromethyl, trifluoromethoxy, difluoromethoxy or methylthio;

Y is F, $CF_3$, $CF_2Cl$, $CF_2H$, $OCF_3$, $OCF_2Cl$, $C_1$–$C_4$-alkyl or $C_1$–$C_4$-alkoxy;

x is $C^1$–$C_2$-alkoxy, $C^1$–$C_2$-alkyl, $C_1$–$C_2$-alkylthio, $C_1$–$C_2$-alkylamino, di-$C_1$–$C_2$-alkylamino halogen, $C_1$–$C_2$-haloalkyl, $C_1$–$C_2$-haloalkoxy, R is hydrogen or methyl;

$R^{19}$ is $C^1$–$C_4$-alkyl, $C_2$–$C_4$-alkenyl, $C_2$–$C_4$-alkynyl or $C_3$–$C_6$-cycloalkyl, each of which can have attached to it 1 to 5 halogen atoms; in the event that E is O or $NR^{20}$, $R^{19}$ is furthermore also methylsulfonyl, ethylsulfonyl, tnfluoromethylsulfonyl, allylsulfonyl, propargylsulfonyl or dimethylsulfamoyl;

$R^{20}$ is hydrogen, methyl or ethyl;

$R^{12}$ is a $C_1$–$C_4$-alkyl group which can have attached to it up to three of the following radicals: halogen, $C_1$–$C_4$-alkoxy, allyl or propargyl;

$R^{17}$ is a $C_1$–$C_4$-alkyl group which can have attached to it one to three of the following radicals: halogen, $C_1$–$C_4$-alkoxy, allyl or propargyl;

$R^{15}$ is hydrogen, a $C_1$–$C_2$-alkoxy group or a $C_1$–$C_4$-alkyl group;

$R^{16}$ is hydrogen or a $C_1$–$C_4$-alkyl group;

$R^{13}$ is H, $C_1$–$C_4$-alkyl or $C_1$–$C_4$-Alkoxy:

$R^{14}$ is $C_1$–$C_4$-alkyl;

n is 1–2; and

Z is N, CH.

3. A solid mixture as claimed in claim 1, comprising an additional herbicidally active ingredient.

4. A solid mixture as claimed in claim 1, comprising 0.5 to 75% by weight of component a).

5. A solid mixture as claimed in claim 1, comprising 1 to 50% by weight of component b).

6. A method of controlling undesirable vegetation, which comprises treating the plants and/or the area to be kept free from the plants with a herbicidally active amount of a solid mixture as claimed in claim 1.

7. A process for the preparation of herbicidal formulations, which comprises mixing a sulfonylurea with an alkyl ether of a copolymer of $C_2$–$C_4$-alkylene oxides.

* * * * *

UNITED STATES PATENT AND TRADEMARK OFFICE
CERTIFICATE OF CORRECTION

PATENT NO. : 6,242,382 B1
DATED : June 5, 2001
INVENTOR(S) : Bratz et al.

It is certified that error appears in the above-identified patent and that said Letters Patent is hereby corrected as shown below:

Title page,
Item [57], Abstract,
Line 1, "ixture" should be -- mixture --.

Column 18, claim 2,
Line 1, "x" should be -- X --.
Line 1, "$C^1$-$C_2$-alkyl" should be -- $C_1$-$C_2$-alkyl --.
Line 5, "$C^1$-$C_4$-alkyl" should be -- $C_1$-$C_4$-alkyl --.
Line 10, "tnfluoromethylsulfonyl" should be -- trifluoromethylsulfonyl --.
Line 25, "Alkoxy" should be -- alkoxy --.

Signed and Sealed this

Thirteenth Day of November, 2001

Attest:

NICHOLAS P. GODICI
Attesting Officer    Acting Director of the United States Patent and Trademark Office